Figure 1:
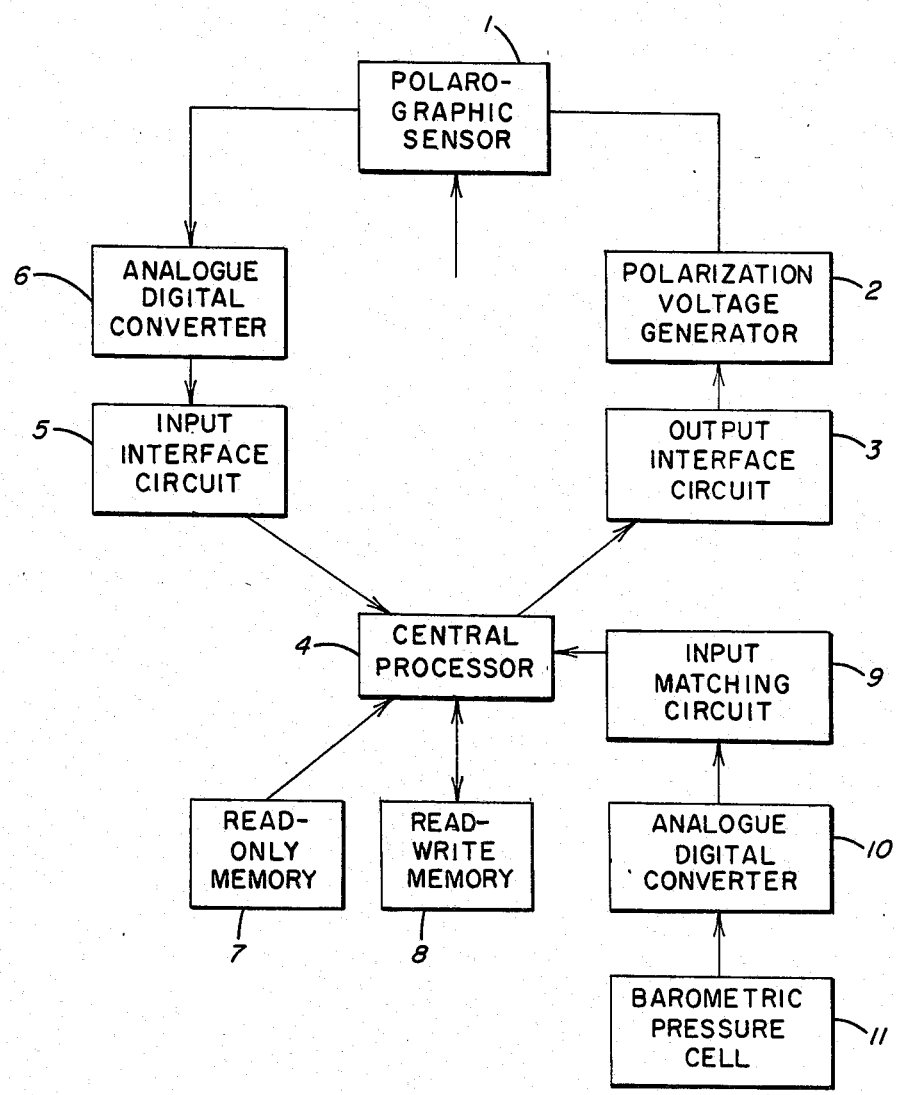

United States Patent [19]

Diskowski et al.

[11] Patent Number: 4,674,061
[45] Date of Patent: Jun. 16, 1987

[54] METHOD AND DEVICE FOR THE AUTOMATIC CALIBRATION OF MEASURING AND INDICATING APPLIANCES FOR THE DETERMINATION OF PARTIAL PRESSURE OF A GAS

[75] Inventors: Jörg Diskowski, Freiburg; Wolfgang Jeppel, Umkirch; Hartmut Moisel, Kirchzarten-Burg; Hans P. Spiess, Umkirch, all of Fed. Rep. of Germany

[73] Assignee: Hellige GmbH, Freiburg, Fed. Rep. of Germany

[21] Appl. No.: 433,856

[22] Filed: Oct. 12, 1982

[30] Foreign Application Priority Data

Oct. 14, 1981 [DE] Fed. Rep. of Germany ....... 3140875

[51] Int. Cl.[4] ...................... G01N 27/28; G06F 15/46
[52] U.S. Cl. .................................... 364/571; 204/400; 364/558
[58] Field of Search ............... 364/571, 550, 551, 558; 204/400, 401, 415

[56] References Cited

U.S. PATENT DOCUMENTS

| | | | |
|---|---|---|---|
| 3,889,255 | 6/1975 | Pettersen | 364/571 |
| 3,997,420 | 12/1976 | Buzza | 204/415 |
| 4,043,756 | 8/1977 | Sommervold | 364/571 |
| 4,115,230 | 9/1978 | Beckman | 204/400 |
| 4,120,770 | 10/1978 | Kessler | 204/400 |
| 4,384,925 | 5/1983 | Stetter et al. | 204/1 T |

FOREIGN PATENT DOCUMENTS 2054169 2/1981 United Kingdom .

Primary Examiner—Felix D. Gruber
Assistant Examiner—H. R. Herndon

[57] ABSTRACT

The method and the device based on it for the automatic calibration of measuring and indicating appliances used for the measurement and indication of the oxygen partial pressure in connection with polarographic sensors provide that a variable polarization voltage supplied by a polarization voltage generator (2), controlled by a central processor (4), is applied to a polarographic sensor (1). The resulting measuring signals of the sensor (1), after analog-digital conversion, are stored in a read-write memory (8). By comparing these with the desired current values stored in a read-only memory (7) the central processor (4) determines the theoretical residual current deviation from the zero value, which in turn is stored. The operating point is fixed at the point of the lowest slope within the operating range of the characteristic line. The theoretical value of the oxygen partial pressure is extrapolated to 100% relative humidity for the chosen sensor temperature with the aid of a signal proportional to the air pressure.

The automatic calibration completely relieves the appliance user of the tedious and time-consuming calibration procedure.

8 Claims, 3 Drawing Figures

POLAROGRAPHIC SENSOR CHARACTERISTICS ———

EXPERIMENTALLY DETERMINED LIMITS — — —

METHOD AND DEVICE FOR THE AUTOMATIC CALIBRATION OF MEASURING AND INDICATING APPLIANCES FOR THE DETERMINATION OF PARTIAL PRESSURE OF A GAS

This invention relates to medical devices of the type employing a polarographic sensor. Such devices are used, for example, to determine the partial pressure of blood gases such as oxygen and carbon dioxide.

BACKGROUND OF INVENTION

As is known in the art, a polarographic sensor comprises an anode and cathode which are electrochemically coupled, via an electrolyte, which is pH-sensitive to the determined gas. Specifically, the pH of the electrolyte is generally proportional to the concentration of the determined gas contained in the gas sample to which the sensor is exposed. Because the current flow from cathode to anode varies with the pH of the electrolyte, one may theoretically impress a constant voltage between the two electrodes and monitor the changing current to determine the pH and, accordingly, partial gas pressure.

The present invention is more particularly related to a method and apparatus for automatically calibrating medical devices employing a polarographic sensor. The sensor's properties change over time, adversely effecting the correlation between pH and gas pressure. These changes are caused, for example, by ambient conditions such as barometric pressure, temperature, and relative humidity. Long-term changes also occur, owing to, inter alia, the drying out of the electrolyte.

Because of the complex chemical-physical relationship underlying the relationship between electrolyte pH and partial pressure of the gas to be determined, the calibration procedure and calibration maintenance of such instruments is a time-consuming operation requiring skilled personnel.

DESCRIPTION OF THE PRIOR ART

Examples of known calibration methods are described in German Patent No. 2,608,727 and German Offenlegingsschrift No. 2,945,207. Both methods require reference or auxiliary gases in the disclosed calibration procedures.

An electronic calibration method for potentiostatic and polarographic sensors is disclosed in German Auslegeschrift No. 2,929,387 wherein the calibration requires a test gas or auxiliary gas and the intervals between calibrations are extended by comparing the activity of the utilized electrode pair with that of a freshly calibrated electrode pair at a prescribed point on the operating curve of the sensor.

SUMMARY OF THE INVENTION

This invention provides a method and apparatus for automatically calibrating a measuring and indicating appliance which uses a polargraphic sensor to determine the partial pressure of a gas. Briefly, a polarization voltage is generated which increases at a constant rate from a preset initial value to a preset maximum value. The polarization voltage is applied to the sensor and the actual values of the resulting sensor current are stored in a read-write memory.

Upon reaching the maximum value, the polarization voltage is decreased at a constant rate back to the initial value and current values are similarly stored.

The actual values of the current are compared by a central processor with desired current values stored in a read-only memory. The desired current values are empirically derived from a multitude of polarograms.

The operating point of the sensor is determined by the central processor unit as the region of minimum slope on the polarogram for the utilized sensor which is stored in the read-write memory.

The theoretical residual current deviation of the sensor from the zero value is determined by the central processor unit in accordance with the difference between the actual and desired current values.

The central processor unit additionally adjusts the actual current value to account for the 100% relative humidity to which the sensor is exposed during actual operation.

By means of this invention, each sensor can be repeatedly calibrated by unskilled personnel and the calibration is specific to each sensor used.

For a more detailed understanding of the invention, reference should be made to the following Description of The Preferred Embodiment, of which the accompanying drawing forms a part.

Figure 2:
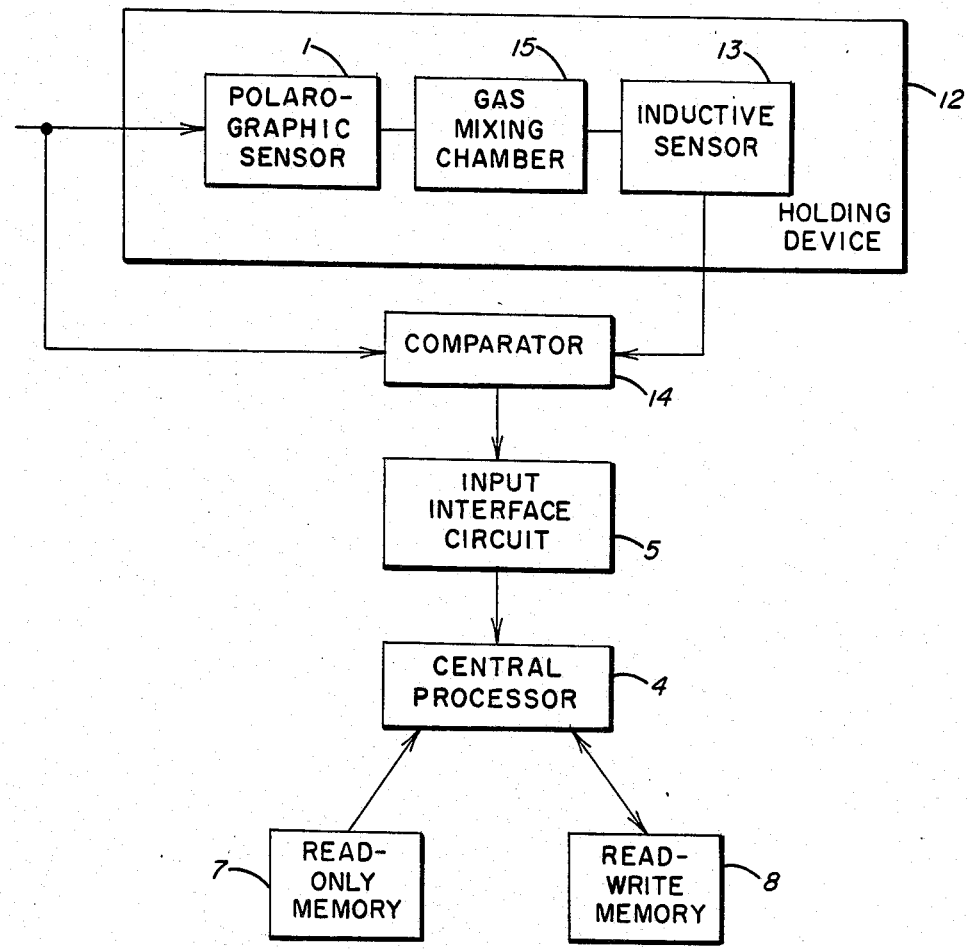
Figure 3:
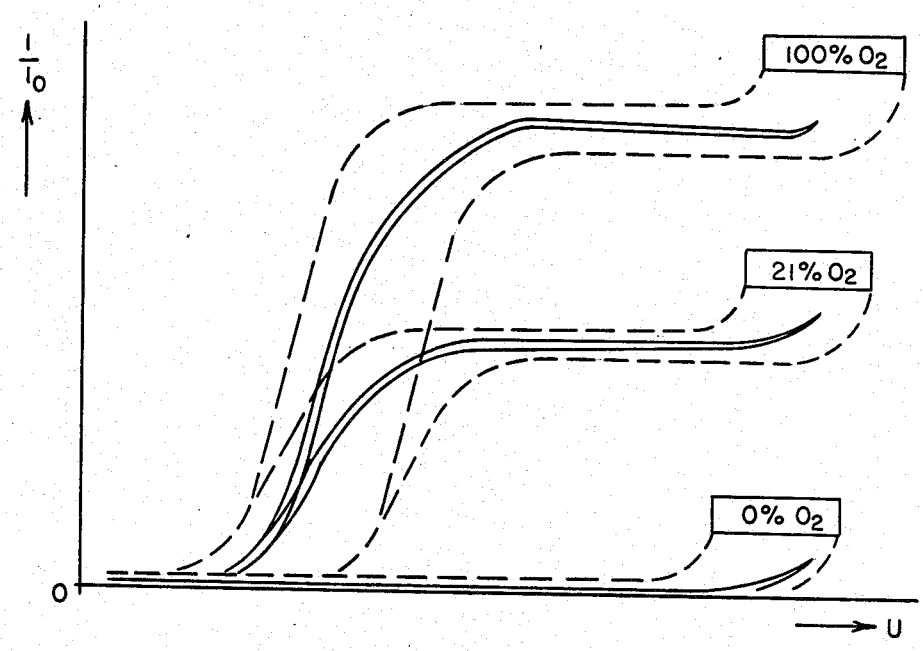

In the drawing,

FIG. 1 is a block diagram of an automatic calibration system constructed in accordance with the invention, FIG. 2 is a block diagram of an additional feature in accordance with the invention which assures calibration of the proper device and/or sensor and FIG. 3 is a graphical illustration of the actual and limiting polarograms stored in memory in accordance with the invention.

In accordance with the invention and as shown in FIG. 1, a central processor 4 acts, via an output interface circuit 3 and a polarization voltage generator 2, on a polarographic sensor 1, the output, or polarization, signal of which, after conversion in an analog-digital converter 6, passes via an input interface circuit 5 to the central processor 4, which passes it on for storage to a read-write memory 8. The output signal of a barometric pressure cell 11, after conversion in an analog-digital converter 10, passes to the central processor 4 via an input matching circuit (interface) 9. A limit polarogram is stored in a read-only memory 7 for comparison with the actual value polarogram.

The sensor 1 is arranged in a known manner for determining the oxygen partial pressure; it is provided with an arrangement for heating the sensor itself and the object to be measured adjacent to the measuring surface of the sensor.

After the central processor 4, in a manner still to be described, has been given a starting signal for the automatic calibration procedure, it provides a control signal to the output interface circuit 3. The output interface circuit 3 causes a polarization voltage generator 2 to supply a variable polarization voltage to the sensor 1.

The waveform of the variable polarization signal is generally of triangular shape, starting with a suitable initial value the polarization voltage increases at a constant rate of millivolt/second, (preferably of 0.5 volt to 2.0 volt) which can be preset. After reaching the maximum value the polarization voltage preferably decreases at the same, and again, constant rate, at which it was increased in the first instance, back to the initial value. The initial value can, for instance, be 0.05 volt. It should be emphasized, however, that the initial value depends upon the type of sensor, upon its temperature, and upon other parameters.

In a preferred embodiment of the invention, it is desirable, in order to save time in carrying out the calibration procedure, to allow the variable polarization voltage to increase or decrease at the above-mentioned rate of increase or decrease only within certain ranges of the characteristic line which are particularly important form the measurement point of view and to tance the other ranges of the characteristic line with an increased rate of change in the increasing or decreasing direction. Stepwise changes of the polarization voltage in the increasing or decreasing direction can also be envisaged within the ranges of the characteristic line, where the progression of the sensor-specific polarogram can be predetermined with a high degree of probability from the progression of the limit polarogram still be be described.

In response to the application of the varying polarization voltage, the polarographic sensor 1 produces a current whose value for each applied voltage level may vary from sensor to sensor. The resulting sensor-specific polarization signal is applied to the input of the analogdigital converter 6 and the digitalized measuring signal of the sensor 1 passes via an input interface circuit 5 to the central processor 4, which passes it on for storage to a read-write memory 8. The stored data forms, in effect, a polarogram which is uniquely characteristic of the sensor hardware operating as sensor 1.

In the read-only memory 7, digital-values representing a limiting polarogram have been stored. These values have previously been determined experimentally by comparative measurements from a multitude of polarograms and programmed within the read-only memory 7 in a suitable digital format in the course of the manufacturing process of the measuring and indicating appliance.

FIG. 3 shows a plot of the ratio of the polarization current I to the saturation current value $I_o$ against the polarization voltage U. FIG. 3 shows the typical progression of the polarogram of the same polarographic sensor 1 for three different values of the oxygen partial pressure, namely 0 % $O_2$, 21% $O_2$ (ambient air) and 100% $O_2$. The relevant tolerance bands of the limit polarogram already described are shown in each case in dashed lines.

The central processor 4 compares the sensor-specific polarogram stored in the read-write memory 8 with the limiting polarogram stored in the read-only memory 7. The central processor 4 calculates the sensor-specific theoretical residual current deviation from the zero point at different points of the characteristic line of the sensor 1 and passes the calculated values into respectively provided storage areas in the read-write memory 8.

During this comparison, sensor-specific polarograms which fall outside the tolerance band inherent in the limiting polarogram are recognized so that defective sensors can be recognized and discarded. In addition to calibration of the sensors, the operating point on the characteristic line is automatically fixed at the location on the polarogram having the least slope. The last-named fixing of the polarization voltage ensures that the sensor current will be minimally effected by small changes in polarization voltage, if any, during operation.

As part of the complete calibration procedure, the central processor 4 calculates the theoretical value of the oxygen partial pressure at 100% relative humidity which, as mentioned, is assumed to be present on the patient's body underneath the measuring surface of the sensor 1 which in use.

Accordingly, a barometric pressure cell 11 is responsive to the air pressure of the ambient air to produce an air pressure signal which is coupled through a converter 10 as a proportional digital signal to the central processor 4 via an input interface circuit 9.

In accordance with the invention, the polarographic sensor 1 is placed within a holding device 12 (FIG. 2) during the automatic calibration procedure, which holding device is attached to the face plate of the measuring and indicating appliance.

It is highly desirable to ensure that an automatic calibration procedure is triggered only if the sensor 1 attached to the measuring and indicating appliance is in the holding device 12. Faulty calibrations, with possibly dangerous consequences could occur if the sensor 1 is not fixed in the holding device 12 during the calibration procedure or if a second sensor from another device has been erroneously placed in the holding device 12.

Built into the sensor 1 in a known manner, not shown, is an arrangement for the electric heating of the sensor and, consequently, of the object to be monitored. The sensor is heated by means of a pulse-shaped current. A temperature sensor, also not shown, measures the temperature of the sensor 1 and controls the temperature of the sensor via a closed control circuit, for instance, by means of pulse-width modulation.

A magnetically responsive sensor 13, arranged in the holding device 12, senses the magnetic fields emanating from the heating current of the sensor and passes the corresponding signal to a comparator 14. The sensor 13 can, for instance, be an inductive sensor, but other magnetic field-sensitive sensors can also be envisaged. The comparator 14 compares the electrical signals sensed by the inductive sensor 13 with the heating current pulses which are given off by the measuring and indicating appliance to the heating current circuit of the sensor 1 and, if both signals are within a predetermined phase relationship, passes a starting signal for a start of the automatic calibration procedure to the central processor 4 via the input of the input matching circuit 5. If the comparator 14 cannot find the coincidence of the two signals, indicating that the sensor 1 is not in the holder 12, calibration procedure will not take place and a warning may be displayed if so desired.

As also shown in FIG. 2, for calibration of the sensor with anaesthetic gases, a gas mixing chamber 15 integral with the measuring and indicating appliance has an outlet adjacent to the measuring surface of the sensor 1 when the sensor is in the holding device 12. Thus, in a varient of the calibration method, the sensor 1 in the holding device 12 at the face plate of the measuring and indicating appliance can be calibrated with a reference gas or mixed gas, such as $N_2O$, from the gas mixing chamber 15. The gases required for the calibration can be supplied to the measuring and indicating appliance by means of suitable connections not shown in the Figures, e.g., from the fixed gas-supply lines of the hospital. A polarogram is traced in a manner already described while mixed gas flows over the sensor. On the characteristic line of the sensor that point is selected as the operating point at which the characteristic operating line has reached a defined slope, starting from its minimum value. After the polarogram has been determined in the manner described above, the measuring surface of the sensor 1 is exposed to the ambient air (21% $O_2$), a further polarogram for the oxygen partial pressure of the ambient air is determined with the polarization voltage fixed according to the above method and this polarogram is then extrapolated to 21% $O_2$.

While the foregoing specification describes a preferred embodiment of the invention, it is recognized that many modifications and variations may be made by those skilled in the art having the benefit of these teachings. Accordingly, it is intended that the foregoing description be illustrative; the invention is to be defined solely by the claims appended hereto which should be given the broadest scope and interpretation possible in view of the prior art.

We claim:

1. A method for the automatic calibration of measuring and indicating appliances for the determination of oxygen partial pressure by means of a sensor, comprising the steps of:
    applying a polarization voltage to said sensor, which polarization voltage increases at a constant pre-determined rate from an initial pre-selected value to a maximum, pre-selected value;
    decreasing the polarization voltage applied to said sensor from said maximum value to said initial value at said constant rate;
    measuring the current flow in said sensor as it corresponds to each value of the polarization voltage applied thereto;
    storing the measured values of the current flow corresponding to the polarization voltages in a read-write memory thereby forming a voltage-current characteristic polarogram of said sensor;
    determining, by forming the polarograms of a multitude of sensors, a representative range of values of current flow relative to polarization voltages in such sensors;
    storing said representative range of values of current flow in a read-only memory;
    comparing said representative range of values of current flow with said measured value of current flow in a central processor to determine the deviation therebetween;
    determining the theoretical residual current deviation of the sensor from the zero value from knowledge of said deviation;
    storing the value of the residual current deviation in memory for the purpose of fixing the zero point of the sensor;
    setting the operating point of the sensor at the point on the voltage-current characteristic line of the sensor where the rate of change of said voltage-current characteristic line is lowest;
    measuring the barometric air pressure of the ambient air; and
    extrapolating the theoretical value of the oxygen partial pressure in the ambient air to that at 100% relative humidity.

2. The method according to claim 1, further comprising the steps of:
    causing a gas mixture to flow over the measuring surface of said sensor;
    forming a polarogram while said gas mixture flows over said sensor;
    determining the point on the characteristic line of said sensor at which, starting from the minimum value, a defined pre-selected slope is reached;
    stopping the flow of said gas mixture over said sensor;
    exposing the measuring surface of said sensor to ambient air;
    forming a second polarogram corresponding to the oxygen partial pressure of ambient air with the polarization voltage corresponding to that at the determined point; and
    extrapolating said second polarogram to 21% oxygen content.

3. A method according to claim 1 wherein said polarization voltage applied to said sensor is at said constant pre-determined increasing and decreasing rate only in a selected range of said polarogram and said polarization voltage increases and decreases at a second constant, greater, rate outside said selected range.

4. A method according to claim 1 wherein the polarization voltage is varied step-wise in pre-selected ranges of the characteristic line of the sensor, whereby the progression of the sensor specific polarogram can be predicted by comparison with said limiting polarogram.

5. A device for the automatic calibration of measuring and indicating appliance for the determination of oxygen partial pressure by means of a sensor comprising:
    a central processor;
    polarographic sensor means;
    a polarization voltage generator coupled between an output of said central processor and an input of said polarographic sensor whereby said central processor controls the output of said generator so as to cause a polarization voltage provided by said generator and applied to said polarographic sensor to increase at a constant rate from an initial value to a maximum pre-selected value and to thereafter decrease at a rate equal to the rate of increase;
    converter means coupling an output of said polarographic sensor to an input of said central processor whereby the output of said sensor is converted to digital form and is provided to said central processor; and
    a barometric pressure cell, the output of which is coupled to an input of said central processor whereby the values of ambient air pressure are provided to said central processor;
    a signal corresponding to a limiting polarogram formed from a plurality of polarograms is stored in a read-only memory portion of said central processor;
    the signal corresponding to said limiting polarogram is compared, in the central processor, with the signal which is provided to said central processor by said polarographic sensor via said converter means;
    the theoretical residual current deviation of the polarographic sensor from the zero value is determined by the central processor based on said signal comparison in said central processor;
    the value of the residual current deviation is stored in a read-write memory portion of said central processor for fixing the zero point of the polarographic sensor;
    the operating point of the polarographic sensor is fixed at the point where the voltage-current characteristic of said polarographic sensor has the lowest slope within a selected range; and the theoretical value of the oxygen partial pressure of the ambient air is extrapolated to 100% relative humidity for the selected temperature of the polarographic sensor utilizing the barometric air pressure signal provided to the central processor by said barometric pressure cell.

6. A device according to claim 5 further comprising;
heating means coupled to said polarographic sensor for providing a pulse-shaped heating current thereto;
a magnetic-field sensitive sensor, positioned adjacent to said polarographic sensor, for providing an output current related to the heating current applied to said polarographic sensor;
comparator means, one input of which is connected to the heater input of said polarographic sensor for receiving said heating current signal and another input of which is connected to the output of said magnetic field sensor for receiving the output current signal therefrom,
the output of said comparator being coupled to said central processor, and
said comparator being adapted to transmit an automatic calibration trigger signal if the heating current signal and the magnetic field sensor current signal provided to said comparator agree in phase relationship with one another.

7. A device according to claim 6 further comprising a gas mixing chamber, the output of which is provided to the measuring surface of the polarographic sensor whereby a polarogram is formed;
the point on the characterisic line of the polarographic sensor at which, starting from a minimum value, a defined pre-selected slope is reached is determined; and
a second polarogram corresponding to oxygen partial pressure of ambient air with the polarization voltagle corresponding to that voltage at said determined point is formed and the second polarogram is extrapolated to 21% oxygen content.

8. A device according to claim 6 wherein said magnetic-field sensitive sensor is an inductive sensor.

* * * * *